United States Patent [19]

Mitsuno et al.

[11] Patent Number: 5,304,111
[45] Date of Patent: Apr. 19, 1994

[54] THERAPEUTIC MAGNETIC SHEET WITH REPEATED CURVED MAGNETIC AREAS

[75] Inventors: Hiroyuki Mitsuno, Oklahoma City, Okla.; Alexander C. Johnson, Jr., Portland, Oreg.

[73] Assignee: Nikken, Inc., Los Angeles, Calif.

[21] Appl. No.: 901,601

[22] Filed: Jun. 19, 1992

[51] Int. Cl.$^5$ ............................................. A61N 1/00
[52] U.S. Cl. .................................... 600/9; 600/15
[58] Field of Search .................................. 600/9-15

[56] References Cited

U.S. PATENT DOCUMENTS 3,921,620 11/1975 Nakayama .
4,480,596 11/1984 Shumiyashu .
4,489,711 12/1984 Latzke .
4,549,532 10/1985 Baermann .

FOREIGN PATENT DOCUMENTS 0081109  6/1983 European Pat. Off. .............. 600/15
3325935  2/1985 Fed. Rep. of Germany ........ 600/15

Primary Examiner—Lee S. Cohen
Assistant Examiner—John P. Lacyk
Attorney, Agent, or Firm—Marger, Johnson, McCollom & Stolowitz

[57] ABSTRACT

A flexible planar magnetic sheet for therapeutic use has a regular repeating pattern of curved first and second areas of alternating magnetic polarity arranged so that a line traverses a plurality of said curved areas in a majority of possible orientations of the line along the surface plane of the sheet with respect to the pattern. In one embodiment, the pattern comprises an array of polka dot regions of one polarity uniformly sized and spaced on a background of opposite polarity. Alternatively, the pattern can be shaped as a series of interdigitated undulating first and second areas of alternating magnetic polarity. The areas each have curved boundaries defined by wavy lines and a width which varies between a maximum and a minimum proceeding generally lengthwise along the wavy lines of a lengthwise periodicity to define lobe-shaped portions of each area.

10 Claims, 2 Drawing Sheets

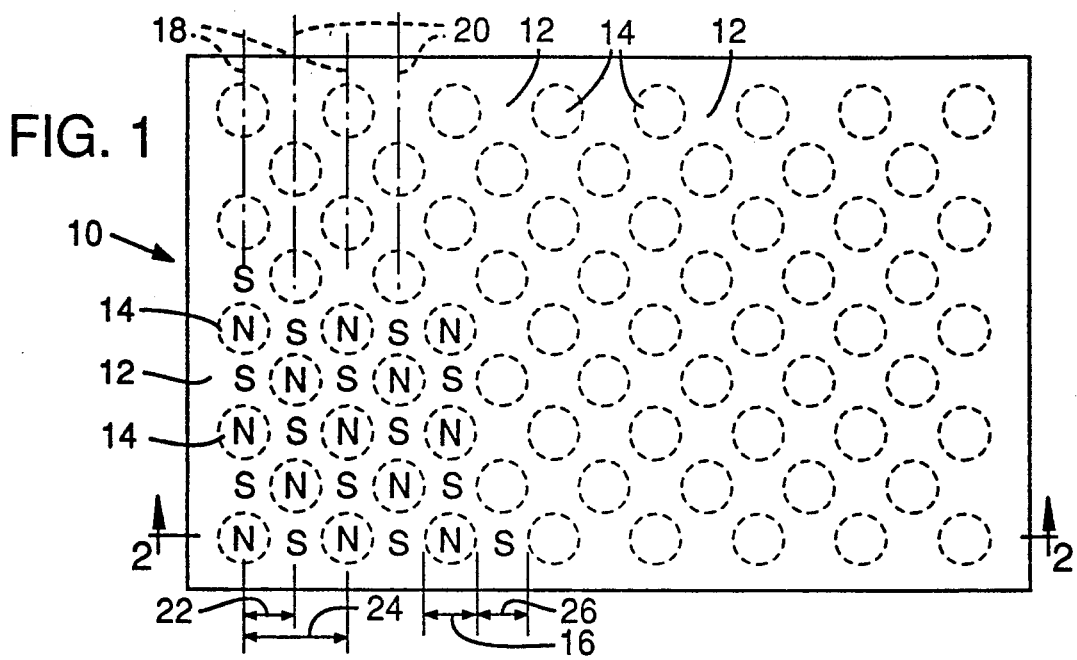
FIG. 1
FIG. 2
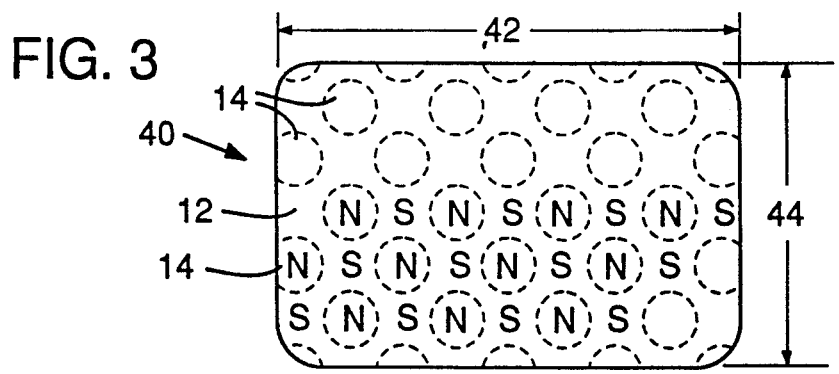
FIG. 3
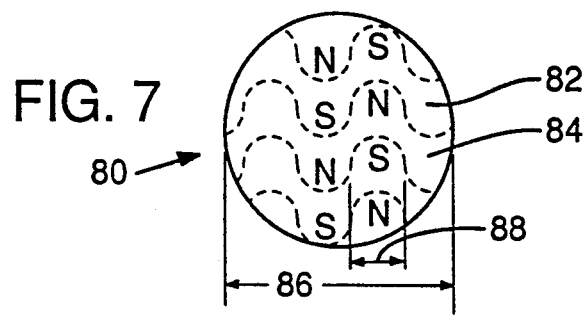
FIG. 7

THERAPEUTIC MAGNETIC SHEET WITH REPEATED CURVED MAGNETIC AREAS

BACKGROUND OF THE INVENTION

1. Field of the Invention

This invention relates generally to magnetic medical treatment aids and more particularly to flexible permanent magnetic sheets having an integrally formed pattern of magnetism for therapeutic use.

2. Description of the Prior Art

Various magnetically patterned sheet-type devices have been disclosed in the prior art as being useful for being applied over a part of a patient's body, the lumbar region for example, to stimulate blood flow and to reduce stiffness and pain. The present invention improves on the prior art in providing these benefits.

U.S. Pat. No. 3,921,620 to Nakayama and U.S. Pat. No. 4,480,596 to Shumiyashu disclose magnetic belts having a pattern of discrete permanent magnet discs received in circular holes arranged in a rectangular pattern in a substrate, such as a flexible magnetic material, for imparting a magnetic flux normal to the material in the lumbar region to reduce stiffness or pain.

U.S. Pat. No. 4,489,711 to Latzke discloses a magnetic plaster formed of an elastic magnetizable plastic sheet material, magnetized in a series of parallel stripes of alternating polarity, at a spacing of 4-10 mm. This arrangement is designed to enable positioning the sheet on the patient's skin with the stripes oriented transversely of the patients vasculature so that blood flow traverses the alternating poles.

U.S. Pat. No. 4,549,532 to Baermann discloses a magnetic sheet which strives to improve upon Latzke's design by arranging the magnetic poles in a pattern which is concentric, angular or radial about a common axis or center. This arrangement is intended to permit the patient to position the sheet in any orientation on the skin and still have the pattern traverse the underlying vasculature. Although an improvement over Latzke's arrangement in this regard, Baermann's approach has several limitations.

First, Baermann's patterns cannot be expanded indefinitely in size to cover large areas of a patient's body. As the pattern is scaled to larger sizes, the circumferential extent of each area of one polarity increases to the point where it is no longer effective to induce any changes in magnetic flux. For example, in the concentric case, each ring becomes very large at a distance spaced from the center, so large that an underlying blood vessel oriented tangentially of the pattern can travel a substantial distance without crossing a magnetic polarity boundary. The same thing can happen in the angular or radial pattern. Additionally, as the angular or radial pattern is enlarged, the lengths of segments increase so that a blood vessel, aligned lengthwise of the segment, does not necessarily cross areas of alternating polarity.

Second, the patterns of both Latzke and Baermann are integrally formed by magnetically imprinting them on the magnetic sheet, using a magnetizing fixture. In the case of Baermann's patterns, it is difficult to make an effective fixture to magnetically imprint these patterns, particularly those having sharp angular intersections between the areas of opposite polarity. It has also been proposed to use a checkerboard polarity pattern. This pattern would also be difficult to build and effective fixture for, because of the large number of right angles packed into a relatively small area. Besides the difficulties in making the fixture, the resulting magnetic fields formed in such small geometries will be blurred at the corners.

Accordingly, a need remains for a design for a therapeutic magnetic sheet having a pattern that will cross underlying vasculature with a high probability over a large area while being oriented freely on a patient's skin, and that is easy to imprint integrally into a flexible magnetic sheet.

SUMMARY OF THE INVENTION

It is, therefore, an object of the invention to pattern a therapeutic magnetic sheet so that it can be oriented freely on a patient's skin and still cross underlying vasculature with a high probability over a large area.

Another object of the invention is to pattern a therapeutic magnetic sheet so that it is easy to imprint integrally into a flexible magnetic sheet.

A further object of the invention is to pattern a therapeutic magnetic sheet with a pattern that is curved and regular over a large area rather than angular or formed in straight lines or arcs of large circumference.

The invention is a flexible planar magnetic sheet for therapeutic use by application to a body surface location, comprising a regular repeating pattern of curved first and second areas of alternating magnetic polarity, the second area having a portion distributed in two dimensions along the surface plane of the sheet among portions of the second area so that a line traverses a plurality of said curved areas in a majority of possible orientations of the line along the surface plane of the sheet with respect to the pattern. The sheet is a flexible sheet composed of a synthetic material having imbedded particles of a permanent magnetic material therein and including a planar skin compatible surface. The magnetic material is magnetized in an orientation normal to the planar surface of the sheet with a first polarity defining the first area and a second polarity opposite the first polarity defining the second area, with a curved boundary between the two areas.

In a preferred embodiment, the pattern comprises a contiguous background magnetization of a first polarity defining the first area and an array of polka dot shaped regions of a second polarity opposite the first polarity defining a plurality of said second areas spaced within the first area. The polka dots are preferably sized and spaced to a uniform diameter and spacing such that the diameter of the polka dots is approximately equal to a portion of the first area defining the spacing among four adjacent polka dots.

Alternatively, each of the curved first and second areas can be shaped as a series of interdigitated undulating areas of opposite magnetic polarity. Each first area of first polarity is bounded along opposite sides by two second areas of second polarity, the curved boundaries between the first and second polarities being defined by wavy lines. The first and second areas each have a width which varies between a maximum and a minimum proceeding generally lengthwise along the wavy lines and defines lobe-shaped portions of each area. The wavy lines have a lengthwise periodicity which defines a length of the lobe-shaped portions of each area. The lobes are preferably sized and spaced to a uniform diameter and spacing such that the dimensions of the lobes in the first area are approximately equal to the dimensions of the lobes in the second area.

The foregoing and other objects, features and advantages of the invention will become more readily apparent from the following detailed description of a preferred embodiment of the invention which proceeds with reference to the accompanying drawings.

BRIEF DESCRIPTION OF THE DRAWINGS

FIG. 1 is a top plan view of a preferred embodiment of a therapeutic magnetic sheet according to the invention.

FIG. 2 is a cross-sectional view taken along lines 2—2 in FIG. 1, wherein vertical cross-hatching is used to show areas of one magnetic polarity.

FIG. 3 is a therapeutic card made using the material of FIGS. 1-2.

FIG. 7 is a circular pad similar to that of FIG. 6 made using an alternative, wavy line pattern.

DETAILED DESCRIPTION

Figure 4:
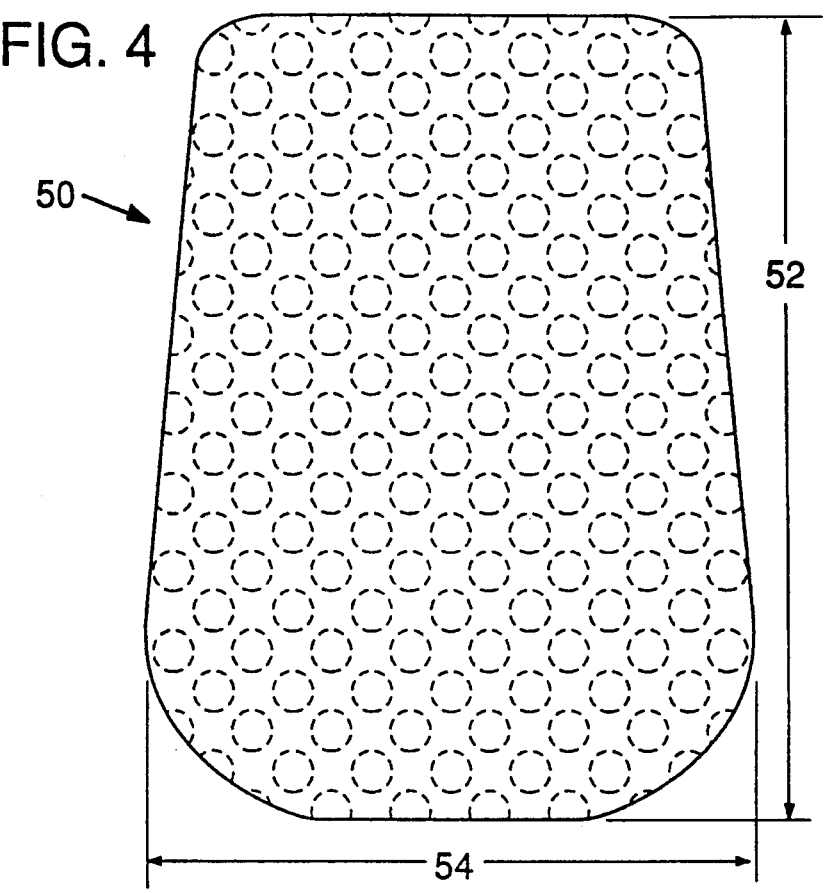
FIG. 4 is a larger area therapeutic pad made using the material of FIGS. 1-2.

Referring to FIGS. 1 and 2, the preferred embodiment of the present invention is a polka dot pattern. This pattern is formed in magnetic sheet 10 on a background forming a first area 12 of one polarity. On this background, a plurality of second areas 14 of a polarity opposite the background polarity is formed by a plurality of circles arrayed on the background area 12. For example, the background or first area 12 can be permanently magnetized to provide a southpole as viewed from the cloth side of the sheet as depicted in FIG. 1, and the polka dot areas 14 can be magnetized to a north polarity.

The circular areas 14 are arranged in a regular rectangular array, preferably oriented diagonally to the edges of the sheet of material. The circles are sized and spaced so that a line drawn at a random orientation across the array has a high probability of crossing both circles 14 and intermittent portions of background area 14, at least a majority of orientations. A preferred diameter 16 for the circles is $\frac{3}{8}$" (9.5 mm). The circles are arranged in even and odd rows 18, 20, which are staggered to form the diagonal pattern. The rows are positioned at a spacing 22 center-to-center of adjacent rows that is equal to the diameter of the circles. Consequently, the even rows 18 have a center-to-center spacing 24 equal to twice the diameter of the circles. Consequently, the edge-to-edge spacing 26 between circles of adjacent even rows or adjacent odd rows is the same as the diameter of the circles, and the odd rows have like spacing. Consequently, polarity area 12 between any four circles 14 has a width 26 in two dimensions of about $\frac{3}{8}$" (9.5 mm).

Referring to FIG. 2, the material used to make the magnetic sheet of the present invention is preferably formed in three layers. The first or innermost layer 30 is a flexible magnetic sheet material into which the pattern of FIG. 1, or a similar pattern, is magnetically imprinted. The sheet material 30 is suitably made of nitrile rubber containing approximately 80% ferric oxide (preferably 1.4 MGO). This flexible ferrite material is provided in a number of commercial products, for example, 3M PLASTIFORM ®. The sheet 10 preferably includes a skin contacting layer 32 which is made of a cotton cloth, adhered to one planar surface of the sheet 30. Preferably, the cotton cloth is positioned on the side of the sheet 30 in which the North pole orientation appears in the circular dots 14. Preferably, a vinyl sheet 34 is adhered to the opposite side of sheet 30. The thickness of sheet 30 can be varied in order to determine the strength of magnetic field, as further described below.

Referring to FIG. 3, one embodiment of the present invention is in the form of a rectangular card or strip 40. Suitable dimensions 42, 44 for the card are $3\frac{1}{4}" \times 2\frac{1}{4}"$ (8.25 cm × 5.4 cm). Alternative dimensions can be used for the rectangular strips, because the polka dot pattern repeats regularly. For example, strips can readily be made 4" (10 cm) or 6" (15 cm) long, or longer, without disrupting the spacing and size of the alternating polarity areas 12, 14. The rows of dots 14 are oriented diagonally with respect to the edges of sheet 10 and the rows of circles 14 are spaced close enough together over the entire extent of the sheet so that a blood vessel traversing any part of the sheet at nearly any orientation has a high probability of crossing alternating polarity areas 12, 14. The only orientation in which it is possible for a line to traverse the polka dot without crossing first and second areas is if the line is aligned along a diagonal between diagonal rows of dots. This is unlikely since the width of the diagonal is only about $\frac{1}{8}$ inch (3.3 mm).

FIG. 4 shows a pad 50 which is larger than card 40 or the longer rectangular strips described above and has an oblong shape. It uses the same magnetization pattern of North polarity polka dots 14 on a South polarity background 12. It has an overall length 52 (e.g. $7\frac{1}{2}$" or 19 cm) and a width 54 (e.g. $5\frac{3}{4}$" or 14.6 cm) at its wider end. The wider end is rounded at the corners with a larger radius than the corners formed at the narrow end of pad 50.

Figure 5:
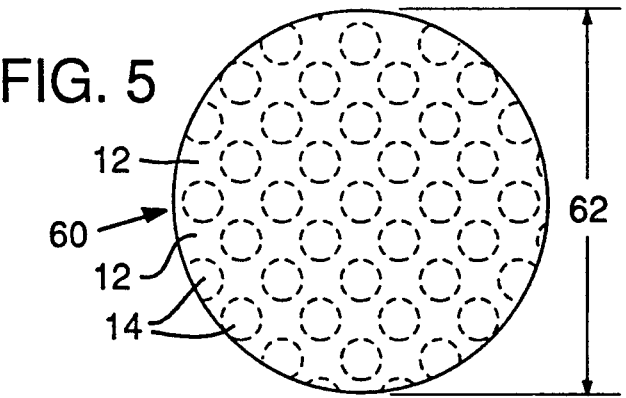
FIGS. 5 and 6 are circular pads of different diameters made using the material of FIGS. 1-3 in different thicknesses.
Figure 6:
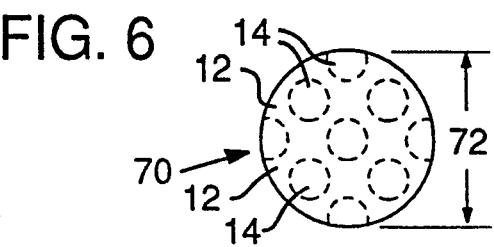

FIG. 5 shows a circular sheet 60 of a diameter 62 (e.g. $3\frac{1}{2}$" or 8.9 cm) and FIG. 6 shows a smaller circular patch 70 with a diameter 72 (e.g. $1\frac{5}{8}$" or 4.1 cm). Both of these patches use the same magnetization pattern 12, 14 as described above but are preferably made in different thicknesses, as further described below.

FIG. 7 shows an alternative pattern 80 in which each of the curved areas of opposite magnetic polarity is shaped as a series of interdigitated undulating first and second areas 82, 84. This pattern is shown in a circular sheet of diameter 86 but can be used in any of the foregoing shapes and sizes of strips and pads, as well as others. Each first area 82 of South polarity is bounded along opposite sides by two second areas 84 of North polarity. The areas of opposite magnetic polarity are demarcated by curved boundaries defined by wavy lines. The wavy lines have a lengthwise periodicity which defines a length of the lobe-shaped portions of each area. The first and second areas each have a width which varies between a maximum and a minimum proceeding generally lengthwise along the wavy lines. This variation in width and the lengthwise periodicity of the wavy lines defines lobe-shaped portions of each area. The lobes are preferably sized and spaced to uniform dimensions 88 and spacing such that the dimensions of the lobes in the first area is approximately equal to the dimensions of the lobes in the second area.

The foregoing patterns are imprinted using a magnetizing fixture designed to create the polka dot or wavy pattern, which is readily within the skill of commercial magnetizers. The patterns are preferably imprinted by magnetizing the sheet material to saturation. The resultant magnetic field is then determined by the thickness and magnetizability of the magnetic sheet material. The card 40 and circular patches 70, 80 are preferably 0.060 inch (1.52 mm) thick, which gives a magnetic field of about 400 Gauss for 1.4 MGO material. The pad 50 is preferably made in a thickness of 0.045 inch (1.14 mm) which gives a magnetic field of 300 Gauss for 1.4 MGO material. The larger circular patch 60 is preferably made in a thickness of 0.030 inch (0.76 mm) which gives a magnetic field of 200 Gauss for 1.4 MGO material. Other thicknesses can be used for different patch sizes and shapes.

Having described and illustrated the principles of the invention in a preferred embodiment thereof, it should be apparent that the invention can be modified in arrangement and detail without departing from such principles. We claim all modifications and variation coming within the spirit and scope of the following claims.

We claim:

1. A flexible magnetic sheet for therapeutic use by application to a body surface location, comprising:
   a flexible sheet composed of a synthetic material having imbedded particles of a permanent magnetic material therein and including a planar skin compatible surface;
   the magnetic material being integrally magnetized in an orientation normal to the planar surface and in first polarity in a contiguous first area and in a second polarity opposite the first polarity in a plurality of second areas spaced apart within the first area;
   each of the second areas being shaped magnetically as a circle bounded by the first area.

2. A flexible magnetic sheet according to claim 1 in which the second areas each have a diameter of about ⅜ inch (9.5 mm).

3. A flexible magnetic sheet according to claim 1 in which the second areas are spaced to define portions of the first area between the second areas of about ⅜ inch (9.5 mm) in length and width.

4. A flexible planar magnetic sheet for therapeutic use by application to a body surface location, comprising:
   a magnetizable flexible sheet having a planar skin compatible surface; and
   the flexible sheet having permanently magnetized portions comprising a regular, translationally repeating pattern of non-concentric curved first and second areas of alternating magnetic polarity permanently magnetized integrally into the sheet;
   the first and second areas being distributed in two dimensions along the skin compatible surface of the sheet so that a blood vessel traverses a plurality of said curved areas regardless of translational position along the surface of the sheet with respect to the pattern.

5. A flexible magnetic sheet according to claim 4 in which the magnetizable flexible sheet is composed of a synthetic material having imbedded particles of a permanent magnetic material therein;
   the magnetic material being magnetized in an orientation normal to the planar surface of the sheet with a first polarity defining the first area and a second polarity opposite the first polarity defining the second area, with a curved boundary between the two areas.

6. A flexible magnetic sheet according to claim 4 in which the pattern comprises a contiguous background magnetization of a first polarity defining the first area and an array of polka dot shaped regions of a second polarity opposite the first polarity defining a plurality of said second areas spaced within the first area.

7. A flexible magnetic sheet according to claim 6 in which the polka dots are sized and spaced to a uniform diameter and spacing such that the diameter of the polka dots is approximately equal to a portion of the first area defining the spacing among four adjacent polka dots.

8. A flexible magnetic sheet according to claim 4 in which the pattern comprises each of the curved first and second areas being shaped as a series of interdigitated undulating areas of opposite magnetic polarity, each first area of first polarity being bounded along opposite sides by two second areas of second polarity, with curved boundaries between the first and second polarities defined by wavy lines.

9. A flexible magnetic sheet according to claim 8 in which the first and second areas each have a width which varies between a maximum and a minimum proceeding generally lengthwise along the wavy lines and defines lobe-shaped portions of each area.

10. A flexible magnetic sheet according to claim 8 in which the wavy lines have a lengthwise periodicity which defines a length and longitudinal spacing of the lobe-shaped portions of each area.

* * * * *

UNITED STATES PATENT AND TRADEMARK OFFICE
CERTIFICATE OF CORRECTION

PATENT NO. : 5,304,111
DATED : April 19, 1994
INVENTOR(S) : Mitsuno, Hiroyuki et al.

It is certified that error appears in the above-identified patent and that said Letters Patent is hereby corrected as shown below:

Drawings,
Fig. 2, replace the drawing below:

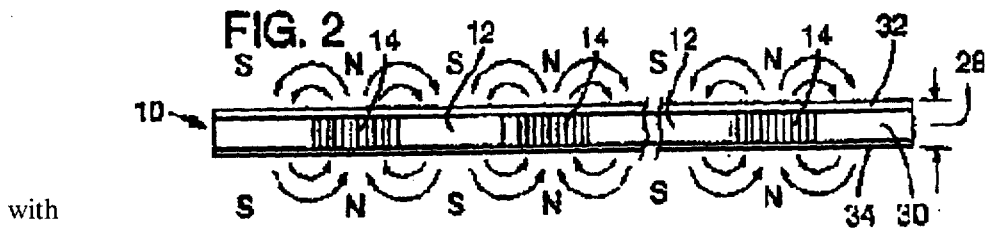

with

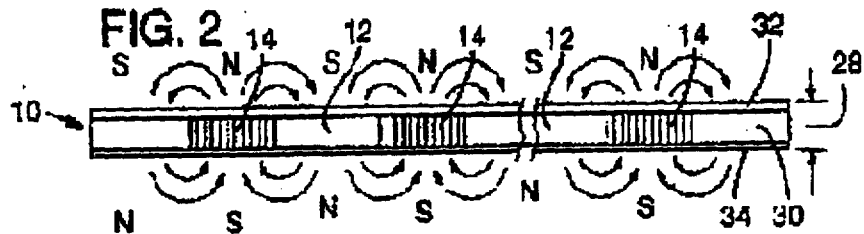

Column 3,
Line 13, replace "show areas of one magnetic polarity" with -- show second areas of the magnetic sheet --

Signed and Sealed this

Twenty-eighth Day of May, 2002

*Attest:*

JAMES E. ROGAN
*Attesting Officer*  *Director of the United States Patent and Trademark Office*